United States Patent [19]
Kim et al.

[11] Patent Number: 6,022,882
[45] Date of Patent: Feb. 8, 2000

[54] 2-CHLORO-3, 5-BIS(TRIFLUOROMETHYL) PHENYL BENZOYL UREA DERIVATIVE AND PROCESS FOR PREPARING THE SAME

[75] Inventors: Jung Ho Kim, Taejon; Yong Woo Shin, Seoul; Jung Nyoung Heo, Taejon; Eui Deok Kim, Taejon; Joon Seo Park, Taejon; Hyun Sam Song, Taejon, all of Rep. of Korea

[73] Assignee: Dongbu Hannong Chemical Co., Ltd., Seoul, Rep. of Korea

[21] Appl. No.: 09/202,814

[22] PCT Filed: Jun. 25, 1997

[86] PCT No.: PCT/KR97/00123

§ 371 Date: Dec. 21, 1998

§ 102(e) Date: Dec. 21, 1998

[87] PCT Pub. No.: WO98/00394

PCT Pub. Date: Jan. 8, 1998

[30] Foreign Application Priority Data

Jun. 29, 1996 [KR] Rep. of Korea .................. 96-26920

[51] Int. Cl.[7] .................. A01N 43/40; A01N 47/28; C07D 211/72; C07C 273/00
[52] U.S. Cl. .................. 514/350; 514/350; 514/594; 546/316; 564/44
[58] Field of Search .................. 564/44; 546/316; 514/350, 594

[56] References Cited

FOREIGN PATENT DOCUMENTS

| | | |
|---|---|---|
| 0093976 | 11/1983 | European Pat. Off. . |
| 0093977 | 11/1983 | European Pat. Off. . |
| 0175416 | 3/1986 | European Pat. Off. . |
| 0232080 | 8/1987 | European Pat. Off. . |
| 0246061 | 11/1987 | European Pat. Off. . |
| 0268952 | 6/1988 | European Pat. Off. . |
| WO94/03066 | 2/1994 | WIPO . |
| 9533711 | 12/1995 | WIPO . |
| WO95/33711 | 12/1995 | WIPO . |

*Primary Examiner*—John Kight
*Assistant Examiner*—Binta Robinson

[57] ABSTRACT

The present invention relates to a novel benzoyl urea derivative which exhibits potent growth-retarding activity against pests and which is represented by formula (I),

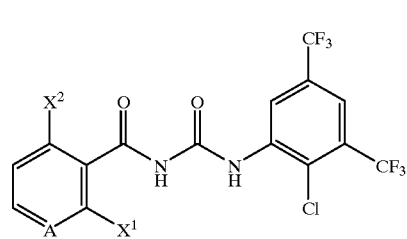

in which A represents N or CH, and $X^1$ and $X^2$ independently of one another represent hydrogen, fluoro, chloro or bromo.

10 Claims, No Drawings

2-CHLORO-3, 5-BIS(TRIFLUOROMETHYL) PHENYL BENZOYL UREA DERIVATIVE AND PROCESS FOR PREPARING THE SAME

This application is the national phase under 35 U.S.C. §371 of prior PCT International Application No. PCT/KR97/00123 which has an International filing date of Jun. 25, 1997 which designated the United States of America.

TECHNICAL FIELD

The present invention relates to a novel 2-chloro-3,5-bis (trifluoromethyl)-phenyl benzoyl urea derivative that exhibits potent growth-retarding activity against insect pests. More specifically, the present invention relates to a novel 2-chloro-3,5-bis(trifluoromethyl)phenyl benzoyl urea derivative represented by the following formula (I):

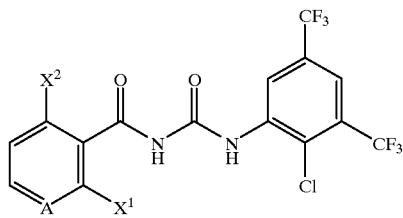

(I)

in which

A represents N or CH, and $X^1$ and $X^2$ independently of one another represent hydrogen, fluoro, chloro or bromo.

The present invention also relates to a process for preparing the compound of formula (I) and a pesticidal composition that includes the compound of formula (I) as an active ingredient.

BACKGROUND ART

Before the present invention was made, several benzoyl urea compounds that inhibit formation of chitin had been developed, including the well known commercial pesticide, N-(2,6-dichlorobenzoyl)-N'-(4-chloro- or 3,4-dichlorophenyl) urea. European Patent Publication Nos. 093,976 and 093,977 disclose 3,5-bis(trifluoromethyl)phenyl benzoyl urea derivatives whose structures are similar to that of the present invention. However, they exhibit weak pesticidal activity against Diamond backmoth even at concentrations as high as 1 ppm. International Publication No. WO 94/03066 teaches a benzoyl ureido pyridyl phenyl ether derivative, which is undesirable because it can be prepared only by means of an intricate and expensive process. European Patent Publication No. 232,080 discloses a 2,5-difluoro4-chlorophenyl benzoyl urea derivative whose $LC_{50}$ value against Tobacco cutworm ranges from 0.3 to 0.4 ppm.

The benzoyl urea derivatives of the prior art thus exhibited weak pesticidal activity only against certain pests, or could be prepared only by means of complicated and uneconomic processes.

DISCLOSURE OF INVENTION

The present inventors had long endeavored to develop a novel benzoyl urea derivative which can be prepared simply and economically and which exhibits pesticidal activity superior to those of existing pesticides that inhibit chitin formation.

The present inventors have discovered that the novel compound of the present invention, 2-chloro-3,5-bis (trifluoromethyl)phenyl benzoyl urea, exhibits pesticidal activity that is suprisingly 25 to 50 times more potent than that of 2-bromo-3,5-bis(trifluoromethyl)phenyl benzoyl urea, which is the subject compound of the International Publication No. WO 95/33711 of the present applicant.

Accordingly, it is an object of the present invention to provide a novel benzoyl urea derivative represented by the following formula (I):

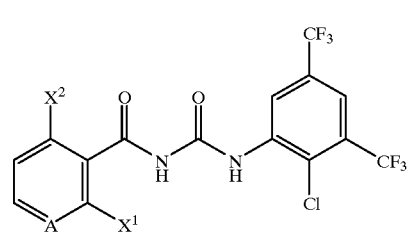

(I)

in which

A represents N or CH, and $X^1$ and $X^2$ independently of one another represent hydrogen, fluoro, chloro or bromo.

It is another object of the present invention to provide a process for preparing the novel benzoyl urea derivative of formula (I):

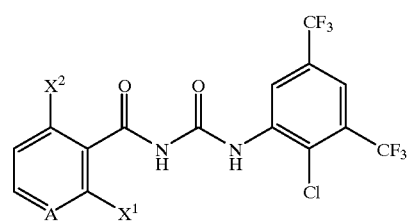

(I)

in which

A represents N or CH, and $X^1$ and $X^2$ independently of one another represent hydrogen, fluoro, chloro or bromo, characterized in that a benzoyl isocyanate represented by the following formula (I):

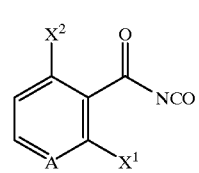

(II)

in which A, $X^1$ and $X^2$ are as previously defined, is reacted with 2-chloro-3,5-bis(trifluoromethyl)aniline represented by the following formula (III):

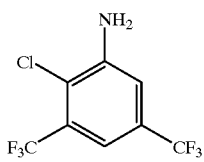

in the presence of a diluent.

It is yet another object of the present invention to provide a pesticidal composition comprising the benzoyl urea derivative of formula (I) as an active ingredient and an agriculturally acceptable carrier.

BEST MODE FOR CARRYING OUT THE INVENTION

The present invention relates to a novel benzoyl urea derivative of the following formula (I) that exhibits potent pesticidal activity:

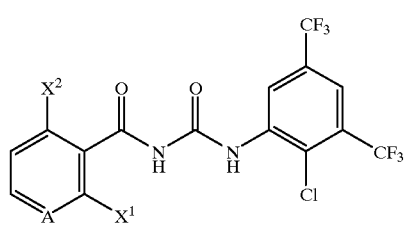

in which

A represents N or CH, and $X^1$ and $X^2$ independently of one another represent hydrogen, fluoro, chloro or bromo.

The compounds represented by formula (I) wherein A represents N or CH, $X^1$ represents fluoro, chloro or bromo, and $X^2$ represents hydrogen, fluoro or chloro are particularly preferred.

Examples of the compound represented by formula (I) include

1-[2-chloro-3,5-bis(trifluoromethyl)phenyl]-3-(2,6-difluorobenzoyl)urea;

1-[2-chloro-3,5-bis(trifluoromethyl)phenyl]-3-(2-fluorobenzoyl)urea;

1-[2-chloro-3,5-bis(trifluoromethyl)phenyl]-3-(2-chlorobenzoyl)urea;

1-[2-chloro-3,5-bis(trifluoromethyl)phenyl]-3-(2-chloronicotinoyl)urea;

1-[2-chloro-3,5-bis(trifluoromethyl)phenyl]-3-(2,6-dichlorobenzoyl)urea; and

1-[2-chloro-3,5-bis(trifluoromethyl)phenyl]-3-(2-bromobenzoyl)urea.

The present invention also relates to a process for preparing the compound of formula (I), wherein the benzoyl isocyanate of formula (II) is reacted with 2-chloro-3,5-bis(trifluoromethyl)aniline in a suitable diluent, according to the following reaction scheme A:

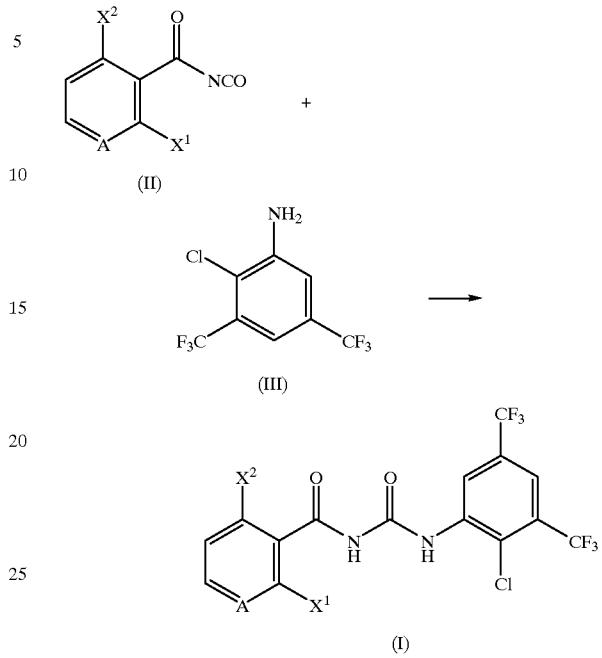

In reaction scheme A, A, $X^1$ and $X^2$ are as previously defined.

In the reaction of the compound of formula (II) with the compound of formula (III) according to the present invention, any inert organic solvent may be used as a diluent unless it adversely affects the reaction. Diluents suitable for this reaction include optionally chlorinated aliphatic or aromatic hydrocarbons such as benzene, toluene, xylene, methylene chloride, chloroform, carbon tetrachloride, 1,2-dichloroethane or chlorobenzene; ethers such as diethylether, dibutylether, tetrahydrofuran or dioxane; ketones such as acetone, methyl ethyl ketone, methyl isopropyl ketone or methyl isobutyl ketone; and nitriles such as acetonitrile or propionitrile. The reaction can be generally carried out under normal pressure at temperature ranging from 0 to 120° C., and preferably ranging from 10 to 50° C.

In this reaction, the reactants are preferably used in equimolar amounts. Although an excess of any one of the reactants may be used, this is not economically advantageous on either an industrial scale or a laboratory scale.

The reaction is practiced at the temperature as defined above by stirring the reactants and the inert diluent for at least 2 hours and then filtering the resulting product in vacuo. The solid obtained after filtration is washed with the diluent used in the previous step or with an alcohol such as methanol, dried, and then recrystallized, if desired, to produce the pure benzoyl urea compound. The product thus obtained is crystalline and has a definite melting point.

The benzoyl isocyanate compound of formula (II) used in the above reaction as the starting material may be prepared by reacting the substituted benzamide or nicotinamide represented by the following formula (IV) with an oxalyl chloride according to well-known processes (see J. Org. Chem. 27, 3742 (1962) or J. Pesticide Sci., 17, 7 (1992)).

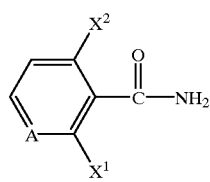

In formula (IV), A, $X^1$ and $X^2$ are as previously defined.

The 2-chloro-3,5-bis(trifluoromethyl)aniline of formula (III) used in the above reaction as a reactant may be prepared according to the known process as depicted in the following reaction scheme B. That is, it may be prepared by reacting 3,5-bis(trifluoromethyl)aniline represented by the following formula (V) with chlorine gas or N-chlorosuccinimide.

Reaction Scheme B

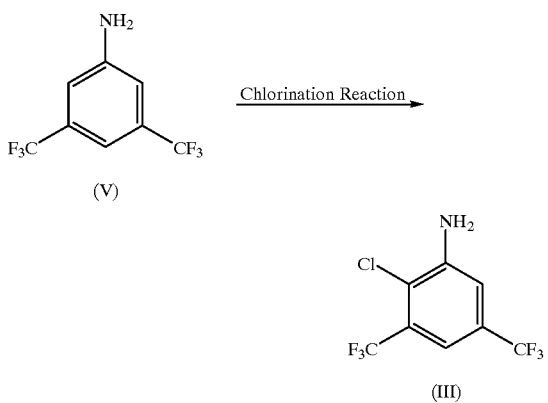

After the above chlorination reaction has gone to completion, the product may be separated and purified by means of well-known methods, such as recrystallization, chromatography, etc.

Typical examples of the novel benzoyl urea derivative of formula (I) prepared according to the present invention are listed in the following Table 1.

TABLE 1

| Com. No. | A | $X^1$ | $X^2$ |
|---|---|---|---|
| 1 | CH | F | F |
| 2 | CH | F | H |
| 3 | CH | Cl | H |
| 4 | N | Cl | H |
| 5 | CH | Cl | Cl |
| 6 | CH | Br | H |

Compound (I) according to the present invention effectively functions as a pesticide by inhibiting chitin synthesis, which in turn inhibits the shedding of the insects' integument, and therefore, is hardly toxic to mammals. The compound of the present invention can be utilized for the protection of farm lands, forests, stored goods, and the like. It is generally effective against not only sensitive or resistant pest species but also insects in all stages of growth.

Pests on which the composition of the present invention is effective include:

Isopoda class, for example, *Onisicus asellus, Airimadillidium vulgare*, anid *Porcellio scaber*; Diplopoda class, for example, *Blaniulus guttulatus*; Chilopoda class, for example, *Geophilus carpophagus* and Scurigera spec.; Symphla class, for example, *Scutigerella immaculata*; Thysanura order, for example, *Lepisma sacchaina*; Collembola order, for example, *Onychiurus armatus*; Orthoptera order, for example, *Blatta orientalis, Periplaneta americana, Leucophaea maderae, Blattela germanica, Acheta domesticus*, Gryllotalpa Spp., *Locusta miigratoria migratorioldes*, Melanoplus differentialis, and *Schistocerca gregaria*; Dermaptera order, for example, *Forficula auricularia*; Isoptera order, for example, Reticulitermes spp.; Anoplura order, for example, *Phylloxera vastratrix*, Pemphigus spp., Pediculus humanus corporis, Haematopinus spp., and Linognathus spp.; Mallophaga order, for example, Trichodectes spp. and Damalinea spp.; Thysanoptera order, for example, *Hercinothrips fomoralis* and *Thrips tabaci*; Heteroptera order, for example, Eurygaster spp., *Dysdercus intermedins*, Piesma Quadrata, *Cimex lectularius, Rhodnius prolixus*, and Triatoma spp.; Homoptera order, for example, *Aleurodes brassicae*, Piesma Quadrata, Trialeurodes vapo rariorum, *Aphis gossypli, Brevicoryne brassicae, Cryptomyzus ribis, Doralis fabae, Doralis pomi, Eriosoma lanigerum, Hyalopterus arundinis, Macrosiphum avenae, Myzus* spp., *Phorodon humuli, Rhopalosiphum padi*, Empoasca spp., *Euscelis bilobatus, Nephotettix cincticeps, Lecanium comi, Saissetia oleae, Laodelphax striatellus, Nilaparvata lugens, Aonidiella aurantil, Aspidiotus hederae*, Pseudococcus spp., and Psylla spp.; Lepidoptera order, for example, *Pectinophora gossypiella, Bupalus piniarius, Cheimatobia brumata, Lithocolletis blancardella*, Hyponomeutapadella, *Plutella maculipennis, Malacosoma neustria, Euproctis chrsorrhoea*, Lymantria spp., *Buccculatrix thurberiella, Phyllocnistis citrella*, Agrotis spp., Euxoa spp., Feltia spp., *Earias insulana*, Heliotibis spp., *Laphygma exigua, Mamestra brassicae, Panolis flammea, Prodenia litura*, Spodoptera spp., *Trichoplusia ni, Carpocapsa pomonella*, Pieris spp., Chilo spp., Pyraustanubilalis, *Ephestia kuehniella, Galleria mellonella, Cacoecia podana, Capua reticulana, Choristoneura fumiferana, Clysia ambiguella, Homona magnanima*, and *Tortrix viridana*; Coleoptera order, for example, *Anobium punctatum, Rhizopertha dominica, Bruchidius obtectus, Acanthoscelides obtectus, Hylotrupes bajulus, Agelastica alni, Leptinotarsa deceimlineata, Phaedon cochleariae*, Diabrotica spp., *Psylliodes chrysocephala, Epilachna varivestis*, Atomiria spp., *Oryzaephilus surinamensis*, Anthonomus spp., Sitophilus spp., *Otiorrhynchus sulcatus, Cosmopolites sordidus, Ceuthorrhynchus assimilis, Hypera postica*, Dermestes spp., Trogoderma spp., Anthrenus spp., Attagenus spp., Lyctus spp., *Meligethes aeneus*, Ptinus spp., *Niptus hololeucus, Gibbium psylloides*, Tribolium spp., *Tenebrio molitor*, Agriotes spp., Conoderus spp., *Melolontha melolontha, Amphimallon soistitialis*, and *Costelytra zealandica*; Hymenoptera order, for example, Diprion spp., Hoplocampa spp., Lasius spp., *Monomorium pharaonis*, and Vespa spp.; Diptera order, for example, Aedes spp., Anopheles spp., Cules spp., *Drosophila melanogaster*, Musca spp., Fannia spp., *Calliphora erythrocephala*, Lucillia spp., Chrysomyia spp., Cuterebra spp., Gastrophilus spp., Hyppobosca spp., Stomoxys spp., Oestrus spp., Hypodrema spp., Tabanus spp., Tannia spp., *Bibio hortulanus, Oscinella frit*, Phorbia spp., *Pegomyia hyoscyami, Ceratitis capitata, Dacut oleae*, and *Tipula paludosa*; Siphonaptera order, for example, *Xenopsylla cheopis* and Ceratophyllus spp.; Arachnida class, for example, *Scorpio maurus* and *Latrodectus mactans*; Acarina order, for example, Acarus siro, Argas spp., Omirithodorus spp., *Dermanyssus gallinae, Eriophyes ribis, Phyllocoptruta oleivora*, Boophilus spp., Rhipicephalus spp., Amblyomma spp., Hyalomma spp., Loxodes spp., Psoroptes spp., Chorioptes spp., Sarcoptes spp., Tarsonemus spp., *Bryobia praetopsa*, Panonychus spp., and Tetranychus spp.

The present invention will be more specifically explained by the following examples. However, it should be understood that the examples are intended to illustrate but not to limit the scope of the present invention in any manner.

EXAMPLE 1
Preparation of 1-[2-chloro-3,5-bis(trifluoromethyl)phenyl]-3-(2,6-difluorobenzoyl)urea In order to synthesize the isocyanate, 1.57 g (10 mmol) of 2,6-difluorobenzamide and 15 ml of dry 1,2-dichloroethane were introduced into a 100 ml flask and then 0.92 g (10.5 mmol) of oxalyl chloride was slowly added thereto at normal temperature by means of a syringe, during which an exothermic reaction occurred that generated hydrochloride gas. The resulting reaction mixture was refluxed for 5 hours and cooled to normal temperature. The reaction solvent and the excess oxalyl chloride were removed therefrom under vacuo to obtain 2,6-difluorobenzoyl isocyanate in an oily state. Thus obtained 2,6-difluorobenzoyl isocyanate was then dissolved in 20 ml of dry 1,2-dichloroethane. Then, 2.63 g of 2-chloro-3,5-bis(trifluoromethyl)aniline was added thereto, reacted for 3 hours, and filtered to obtain 4.15 g (Yield from benzamide, 93%) of the title compound as a solid.

m.p.: 184° C.

EXAMPLE 2
Preparation of 1-[2-chloro-3,5-bis(trifluoromethyl)phenyl]-3-(2-fluorobenzoyl)urea 2-fluorobenzoyl isocyanate was synthesized from 1.4 g of 2-fluorobenzamide according to the procedure described in Example 1. Then, 2.63 g of 2-chloro-3,5-bis (trifluoromethyl)aniline was added thereto in order to obtain 4.1 g (Yield 94%) of the title compound.

m.p.: 140–142° C.

EXAMPLE 3
Preparation of 1-[2-chloro-3,5-bis(trifluoromethiyl)phenyl]-3-(2-chlorobenzoyl)urea 2-chlorobenzoyl isocyanate was synthesized from 1.56 g of 2-chlorobenzamide according to the procedure described in Example 1. Then, 2.63 g of 2-chloro-3,5-bis (trifluoromethyl)aniline was added thereto in order to obtain 4.1 g (Yield 92%) of the title compound.

m.p.: 164–166° C.

EXAMPLE 4
Preparation of 1-[2-chloro-3,5-bis(trifluoromethyl)phenyl]-3-(2-chloronicotinoyl)urea 2-chloronicotinoyl isocyanate was synthesized from 1.56 g of 2-chloronicotinamide according to the procedure described in Example 1. Then, 2.63 g of 2-chloro-3,S-bis (trifluoromethyl)aniline was added thereto in order to obtain 4.1 g (Yield 93%) of the title compound.

m.p.: 160–164° C.

EXAMPLE 5
Preparation of 1-[2-chloro-3,5-bis(trifluoromethyl)phenyl]-3-(2,6-dichlorobenzoyl)urea 2,6-dichlorobenzoyl isocyanate was synthesized from 1.9 g of 2,6-dichlorobenzamide according to the procedure described in Example 1. Then, 2.63 g of 2-chloro-3,5-bis (trifluoromethyl)aniline was added thereto in order to obtain 4.5 g (Yield 95%) of the title compound.

m.p.: 205–210° C.

EXAMPLE 6
Preparation of 1-[2-chloro-3,5-bis(trifluoromethyl)phenyl]-3-(2-bromobenzoyl)urea 2-bromobenzoyl isocyanate was synthesized from 2.0 g of 2-bromobenzamide according to the procedure described in Example 1. Then, 2.63 g of 2-chloro-3,5-bis (trifluoromethyl)aniline was added thereto in order to obtain 4.7 g (Yield 96%) of the title compound.

m.p.: 176° C.

The 2-chloro-3,5-bis(trifluoromethyl)phenyl benzoyl urea derivatives of the present invention prepared according to the procedures described in the above examples show excellent preventive activity against pests and plant-parasitic insects such as Diamond-back moth (*Plutella xylostella*), Tobacco cutworm (*Spodoptera litura*), and Fall army worm (*Spodoptera frugiperda*). Their pesticidal activity can be determined by the following experiments.

The pesticidal compositions used in the experiments described below can be prepared in a variety of formulations according to their purposes. For convenience, the compound of the present invention was mixed with suitable amounts of surfactant, water, and acetone to produce a test preparation containing the test compound in a predetermined concentration. The compound was first tested at a concentration of 250 ppm, and if that concentration was 100% lethal, the concentration was gradually decreased until 50% of the pests were survived (i.e., $LC_{50}$ value).

In order to confirm the strong pesticidal activity of the present compound, the $LC_{50}$ value of the compound according to the present invention was compared with that of the widely-used comparative compounds described in the following Table 2.

TABLE 2

| Comparative Compound | Structure | Name |
| --- | --- | --- |
| (A) | 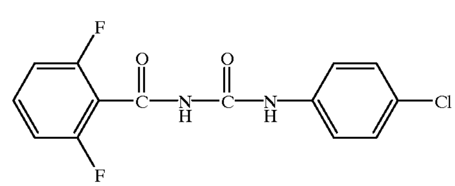 | Diflubenzuron |

TABLE 2-continued

| Comparative Compound | Structure | Name |
|---|---|---|
| (B) | [structure diagram] | Chlorofluazuron |
| (C) | [structure diagram] | |

EXPERIMENT 1

Test for pesticidal activity against Diamond backmoth (*Plutella xylostella*)

Round disks of diameter 5 cm were cut from fresh cabbage leaves. 25 mg of the test compound was dissolved in 100 ml of a mixture containing acetone and aqueous triton-X 100 solution (100 ppm) in the ratio of 1:9 (v/v) to produce a test preparation containing the test compound in the concentration of 250 ppm. The cabbage leaf disks were dipped into the test preparation for 30 seconds and then dried in a hood. The dried cabbage leaf disks were put into a disposable petri dish of diameter 5 cm, into which 20 three-aged larvae of Diamond backmoth (*Plutella xylostelia*) were inoculated using a fine brush. The dish was then tightly sealed with a lid in order to prevent the escape of larvae.

The contents of the petri dish were maintained at 25° C. and 60% humidity. Abnormal growth of Diamond-back moth and lethality of each test compound were examined after 120 hours, and the lethality thus determined at a concentration of 250 ppm is given in the following Table 3.

TABLE 3

| Com. No. | Lethality (%) |
|---|---|
| 1 | 100 |
| 2 | 100 |
| 3 | 100 |
| 4 | 100 |
| 5 | 100 |
| 6 | 100 |

Estimated $LC_{50}$ values for some of the test compounds and comparative compounds are given in the following Table 4.

TABLE 4

| Com. No. | $LC_{50}$ (ppm) |
|---|---|
| 1 | 0.02 |
| 2 | 0.016 |
| 3 | 0.016 |
| (A) | 100~125 |
| (B) | 0.035 |
| (C) | 0.8 |

EXPERIMENT 2

Test for pesticidal activity against Tobacco cutworm (*Spodoptera litura*)

Round disks of diameter 5 cm were cut from fresh cabbage leaves. 25 mg of the test compound was dissolved in 100 ml of a mixture containing acetone and aqueous triton-X 100 solution (100 ppm) in a ratio of 1:9 (v/v) in order to obtain a test preparation of 250 ppm. The cabbage leaf disks were dipped into the test preparation for 30 seconds and then dried in a hood. The dried cabbage leaf disks were put into a disposable petri dish of diameter 5 cm, into which 20 three-aged larvae of Tobacco cutworm (*Spodoptera litura*) were inoculated using a fine brush. The dish was then tightly sealed with a lid in order to prevent the escape of larvae.

The contents of the petri dish were maintained at 25° C. and 60% humidity. Abnormal growth of Tobacco cutworm and lethality of each test compound were examined after 120 hours, and the lethality thus determined at a concentration of 250 ppm is given in the following Table 5.

TABLE 5

| Com. No. | Lethality (%) |
|---|---|
| 1 | 100 |
| 2 | 100 |
| 3 | 100 |
| 4 | 80 |
| 5 | 100 |
| 6 | 100 |

Estimated $LC_{50}$ values for some of the test compounds and comparative compounds are given in the following Table 6.

TABLE 6

| Com. No. | $LC_{50}$ (ppm) |
|---|---|
| 1 | 0.005 |
| 5 | 0.008 |
| (A) | 3.3 |
| (B) | 0.022 |
| (C) | 0.2 |

EXPERIMENT 3

Test for pesticidal activity against Fall army worm (*Spodoptera fruigiperda*)

Round disks of diameter 5 cm were cut from fresh cabbage leaves. 25 mg of the test compound was dissolved in 50 ml of a mixture containing acetone and aqueous triton-X 100 solution (100 ppm) in a ratio of 1:9 (v/v) in order to obtain a test preparation of 500 ppm. The cabbage leaf disks were dipped into the test preparation for 30 seconds and then dried in a hood. The dried cabbage leaf disks were put into a disposable petri dish of diameter 5 cm, into which 20 three-aged larvae of Fall army worm (*Spodoptera frugiperda*) were inoculated using a fine brush. The dish was then tightly sealed with a lid in order to prevent the escape of larvae.

The contents of the petri dish were maintained at 25° C. and 60% humidity. Abnormal growth of Fall army worm and lethality of each test compound were examined after 7 days. In case 100% of lethality was shown, concentration was gradually decreased to 0.1 ppm. The lethality of each test compound at each of several concentrations is given in the following Table 7.

TABLE 7

| Com. No. | Concentration (ppm) | | | | |
|---|---|---|---|---|---|
| | 500 | 100 | 10 | 1 | 0.1 |
| 1 | 100% | 100% | 100% | 100% | 100% |
| 2 | 100% | 100% | 100% | 60% | 20% |
| 5 | 100% | 100% | 90% | 70% | 30% |
| (C) | 100% | 80% | 20% | — | — |

As can be seen from the above experimental results, the benzoyl urea derivative according to the present invention exhibits a pesticidal activity against Diamond backmoth and Tobacco cutworm that is more than 500 times that of diflubenzuron (comparative compound A), which is the most widely-used pesticide that inhibits chitin formation. The benzoyl urea derivative according to the present invention also shows a pesticidal activity superior to that of chlorofluazuron (comparative compound B) and a pesticidal activity against Diamond backmoth and Tobacco cutworm 25 to 50 times that of comparative compound (C), which has a structure similar to that of compounds (A) and (B). As can also be seen from Table 7 above, the compound (1) of the present invention shows an unexpected high lethality of 100% against Fall army worm at a concentration of 0.1 ppm, which is 100 times greater than that of the comparative compound (C). The compound of the present invention has the added advantage of being much more economical to prepare due to the simplicity of its preparation process.

What is claimed is:

1. A 2-chloro-3,5-bis(trifluoromethyl)phenyl benzoyl urea derivative represented by the following formula (I):

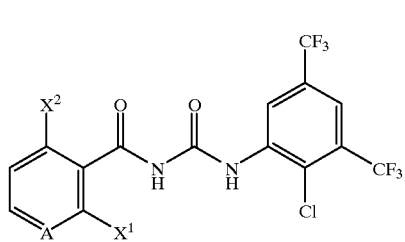

(I)

in which

A represents N or CH, and $X^1$ and $X^2$ independently of one another represent hydrogen, fluoro, chloro or bromo.

2. The 2-chloro-3,5-bis(trifluoromethyl)phenyl benzoyl urea derivative of claim 1, wherein the compound of formula (I) is 1-[2-chloro-3,5-bis(trifluoromethyl)phenyl]-3-(2,6-difluorobenzoyl)urea.

3. The 2-chloro-3,5-bis(trifluoromethyl)phenyl benzoyl urea derivative of claim 1, wherein the compound of formula (I) is 1-[2-chloro-3,5-bis(trifluoromethyl)phenyl]-3-(2-fluorobenzoyl)urea.

4. The 2-chloro-3,5-bis(trifluoromethyl)phenyl benzoyl urea derivative of claim 1, wherein the compound of formula (I) is 1-[2-chloro-3,5-bis(trifluoromethyl)phenyl]-3-(2-chlorobenzoyl)urea.

5. The 2-chloro-3,5-bis(trifluoromethyl)phenyl benzoyl urea derivative of claim 1, wherein the compound of formula (1) is 1-[2-chloro-3,5-bis(trifluoromethyl)phenyl]-3-(2-chloronicotinoyl)urea.

6. The 2-chloro-3,5-bis(trifluoromethyl)phenyl benzoyl urea derivative of claim 1, wherein the compound of formula (I) is 1-[$^2$-chloro-3,5-bis(trifluoromethyl)phenyl]-3-(2,6-dichlorobenzoyl)urea.

7. The 2-chloro-3,5-bis(trifluoromethyl)phenyl benzoyl urea derivative of claim 1, wherein the compound of formula (I) is 1-[2-chloro-3,5-bis(trifluoromethyl)phenyl]-3-(2-bromobenzoyl)urea.

8. A process for preparing 2-chloro-3,5-bis(trifluoromethyl)phenyl benzoyl urea derivative represented by the following formula (I):

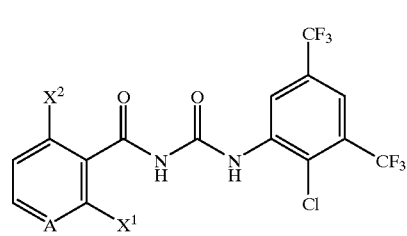

(I)

in which

A represents N or CH, and $X^1$ and $X^2$ independently of one another represent hydrogen, fluoro, chloro or bromo, characterized in that a benzoyl isocyanate represented by the following formula (II):

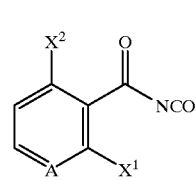

(II)

in which A, $X^1$ and $X^2$ are defined as above, is reacted with 2-chloro-3,5-bis(trifluoromethyl)aniline represented by the following formula (III):

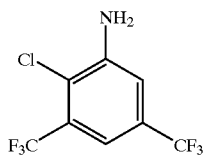

(III)

in the presence of a diluent.

9. The process of claim 8, wherein the diluent is selected from a group consisting of benzene, toluene, xylene, methylene chloride, chloroform, carbon tetrachloride, 1,2-dichloroethane, chlorobenzene, diethylether, dibutylether, tetrahydrofuran, dioxane, acetone, methyl ethyl ketone, methyl isopropyl ketone, methyl isobutyl ketone, acetonitrile and propionitrile.

10. A pesticidal composition comprising an agriculturally acceptable carrier and as an active ingredient a 2-chloro-3,5-bis (trifluoromethyl)phenyl benzoyl urea derivative represented by the following formula (I):

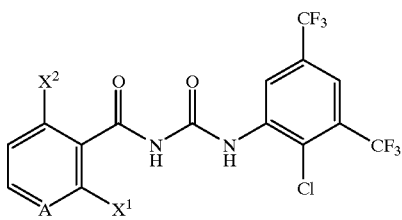

(I)

in which

A represents N or CH, and $X^1$ and $X^2$ independently of one another represent hydrogen, fluoro, chloro or bromo.

* * * * *